United States Patent
Chanduszko et al.

(10) Patent No.: US 10,702,679 B2
(45) Date of Patent: Jul. 7, 2020

(54) BALLOON CATHETER HAVING MULTIPLE INFLATION LUMENS AND RELATED METHODS

(71) Applicant: C.R. BARD, INC., Tempe, AZ (US)

(72) Inventors: Andrzej J. Chanduszko, Chandler, AZ (US); Simon A. Lubek, Tempe, AZ (US)

(73) Assignee: C.R. BARD, INC., Tempe, AZ (US)

( * ) Notice: Subject to any disclaimer, the term of this patent is extended or adjusted under 35 U.S.C. 154(b) by 241 days.

(21) Appl. No.: 15/398,973

(22) Filed: Jan. 5, 2017

(65) Prior Publication Data

US 2017/0113025 A1    Apr. 27, 2017

Related U.S. Application Data

(63) Continuation of application No. 14/403,062, filed as application No. PCT/US2013/062861 on Oct. 1, 2013, now Pat. No. 9,572,960.

(Continued)

(51) Int. Cl.
*A61M 25/10* (2013.01)
*A61F 2/07* (2013.01)
(Continued)

(52) U.S. Cl.
CPC .......... *A61M 25/1018* (2013.01); *A61F 2/07* (2013.01); *A61F 2/86* (2013.01); *A61F 2/915* (2013.01); *A61F 2/958* (2013.01); *A61M 25/09* (2013.01); *A61M 25/104* (2013.01); *A61M 25/1025* (2013.01); *A61F 2002/072* (2013.01); *A61F 2002/91516* (2013.01); *A61F 2002/91558* (2013.01); *A61F 2002/91583* (2013.01); *A61F 2210/0014* (2013.01); *A61F 2230/0054* (2013.01); *A61F 2230/0056* (2013.01); *A61M 2025/105* (2013.01); *A61M 2025/1056* (2013.01); *A61M 2025/1061* (2013.01)

(58) Field of Classification Search
CPC ................ A61M 25/10; A61M 25/104; A61M 25/1025; A61M 25/10181; A61M 25/10182; A61M 25/10183; A61M 2025/1059; A61M 2025/1061; A61M 25/1018; A61F 2/07; A61F 2/86; A61F 2/915; A61F 2/958; A61F 2/09; A61F 2/1025; A61F 2/104
See application file for complete search history.

(56) References Cited

U.S. PATENT DOCUMENTS 5,484,409 A * 1/1996 Atkinson .......... A61M 25/0023
                                                      604/103.03
5,639,274 A * 6/1997 Fischell .................. A61F 2/958
                                                      604/104

(Continued)

*Primary Examiner* — Tuan V Nguyen
(74) *Attorney, Agent, or Firm* — King & Schickli, PLLC

(57) ABSTRACT

An apparatus is for performing a medical procedure using an inflation fluid. The apparatus includes a shaft with two inflation lumens for transmitting the inflation fluid. A balloon supported by the shaft has an interior capable of being inflated by the inflation fluid transmitted through the inflation lumens of the shaft. The tubes defining the inflation lumens provide two outlets for transmitting different flows of the inflation fluid to the interior of the balloon. A stent and related methods are also disclosed.

18 Claims, 6 Drawing Sheets

Related U.S. Application Data

(60) Provisional application No. 61/747,452, filed on Dec. 31, 2012, provisional application No. 61/708,445, filed on Oct. 1, 2012.

(51) Int. Cl.
*A61F 2/915* (2013.01)
*A61F 2/958* (2013.01)
*A61F 2/86* (2013.01)
*A61M 25/09* (2006.01)

(56) References Cited

U.S. PATENT DOCUMENTS

2001/0037081 A1* 11/2001 Heiner .................. A61B 18/02
                                                       604/23
2004/0267280 A1* 12/2004 Nishide ................. A61F 2/958
                                                       606/108
2013/0030520 A1*  1/2013 Lee ..................... A61F 2/2433
                                                       623/2.11

* cited by examiner

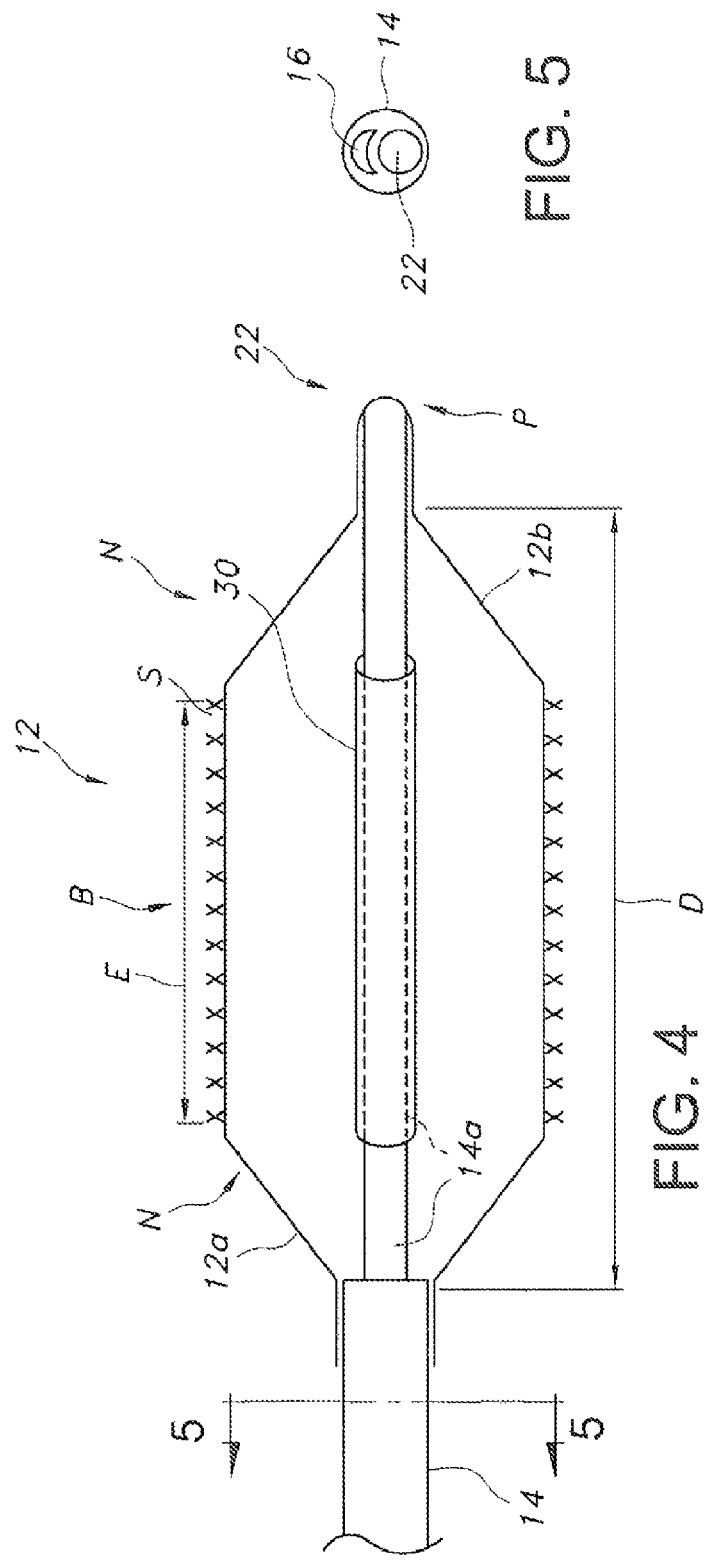
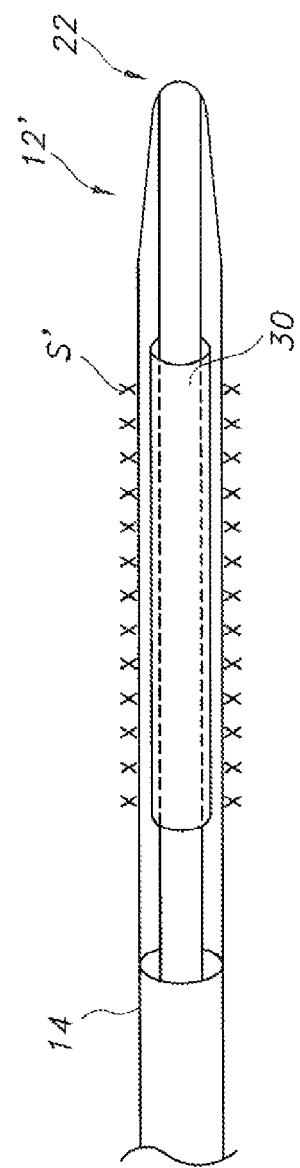

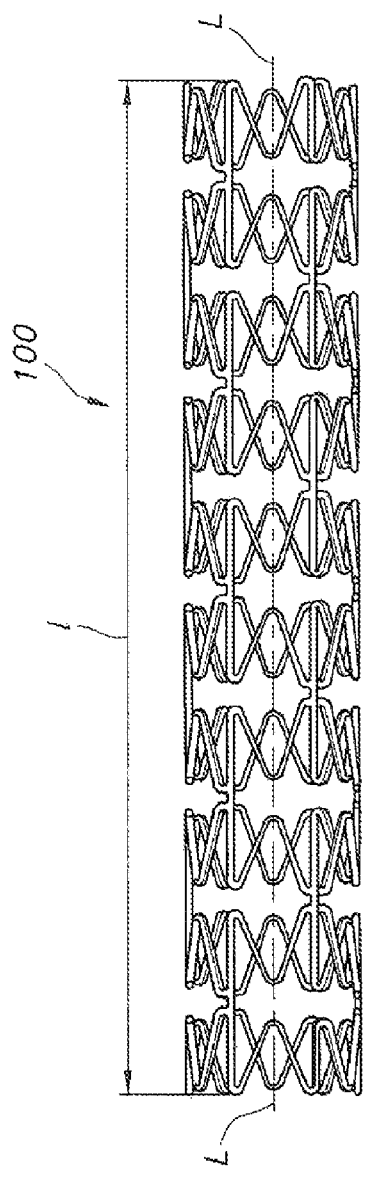
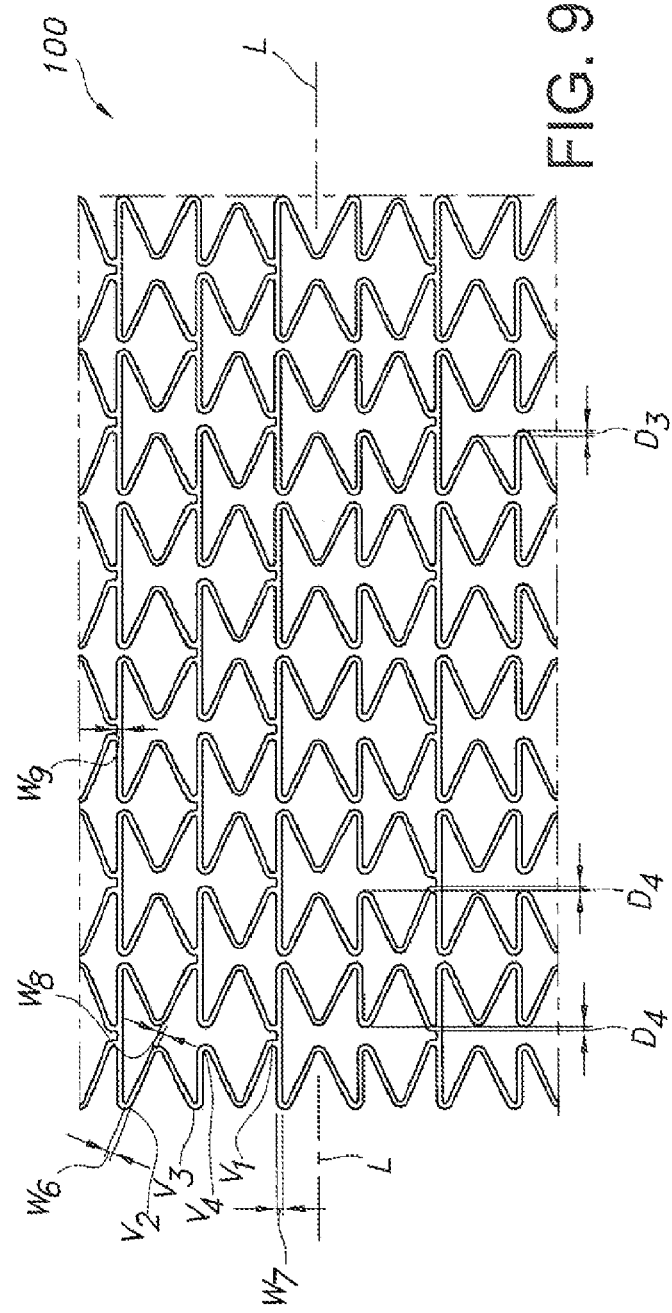

BALLOON CATHETER HAVING MULTIPLE INFLATION LUMENS AND RELATED METHODS

This application claims the benefit of U.S. Provisional Patent Application Ser. Nos. 61/708,445 and 61/747,452, the disclosures of which are incorporated herein by reference.

TECHNICAL FIELD

This disclosure relates generally to an apparatus for performing a medical procedure, such as angioplasty, as well as balloon expandable stent/stent graft delivery. More particularly, this disclosure relates to a balloon catheter with improved inflation characteristics for optimal stent deployment and related methods.

BACKGROUND

Balloon catheters have been devised for use in various medical procedures, including angioplasty and balloon expandable stent/stent graft (implant) delivery. Commonly, a guidewire introduced percutaneously into the patient's vascular system advances via steering to the site of a stenosis. A dilatation balloon on the catheter is advanced over the guide wire until the balloon is positioned within the stenosis (which makes it desirable to provide the balloon with a particularly low profile, yet with adequate strength to be pushed through the vasculature). On inflation, the balloon compresses the stenosis by dilatation of the blood vessel to re-establish a more adequate blood flow path past the stenosis. To facilitate even compression pressure distribution along the length of the stenosed lesion, it is a clinical preference that the dilation balloon be sized and centered relative to the stenosis so as to fully engage the lesion.

Balloon dilation catheters have also been utilized in balloon expandable implant delivery in which the implant is disposed about the balloon and inflated into place at the stenosis. Catheter operators seek accurate deployment of the implant directly on the diseased tissue of the vessel in order to avoid stent migration to either side of the diseased tissue thereby avoiding or minimizing the chance of leaving some of the diseased tissue untreated. Accurate deployment also desirably avoids adversely affecting healthy tissue.

Implant misplacements may occur because of specific inflation dynamics experienced by the expandable balloon when deploying the implant. Many balloon expandable implant delivery catheters inflate the balloon preferentially from the proximal end of the balloon (and may suffer from the inability to transmit inflation fluid from the proximal to the distal end as a result of the placement of the compressed or unexpanded implant over the balloon). During inflation, the expanding balloon may form an asymmetrical growth or inflation wave that may be said to drive or plow the implant so that it opens progressively from one end to the other along the front of the inflation wave. The wave may sometimes cause the implant to disengage prematurely from the balloon, and may also cause a deploying implant to displace longitudinally away from its intended delivery site, thereby potentially ineffectively treating the diseased lesion within the patient's vasculature. This premature deployment is often described as "watermelon seeding." Accuracy of positioning is also important for stents and stent grafts, as missing the target can have deleterious consequences.

Accordingly, a need is identified for a balloon catheter that may be inflated in a preferential manner and with better regulation in order to facilitate the proper delivery of a stent, stent graft, or the like, yet without sacrificing the desire for a low-profile arrangement.

SUMMARY

An object of the disclosure is to provide a balloon catheter that can be inflated in a preferential manner in order to facilitate the proper delivery of a stent, stent graft, or the like.

In one aspect, an apparatus for performing a medical procedure using an inflation fluid comprises an inflatable balloon having an interior for receiving the inflation fluid. A first tube includes a first inflation lumen with a first outlet for transmitting a first flow of the inflation fluid to the interior of the balloon. A second tube positioned at least partially within the balloon includes a second inflation lumen having a second outlet for transmitting a second flow of the inflation fluid to the balloon.

In one embodiment, the first tube further includes a guidewire lumen. The first inflation lumen and the guidewire lumen may be co-axial proximally of the balloon. The first outlet of the first inflation lumen may also be located within a proximal cone of the balloon, and the second outlet of the second inflation lumen may be located within a distal cone of the balloon. In this manner, the preferential inflation to avoid the problem of a stent "watermelon seeding" as a result of an uneven inflation wave (proximal to distal, or vice-versa) may be avoided.

In these or other embodiments, the first tube may extend into the balloon interior a first distance and the second tube may extend into the balloon interior a second distance. The first and second tubes may have different diameters, may comprise different materials, or may include a combination of the two. In any case, the balloon may include a therapeutic agent, a stent, a stent graft, or any combination thereof.

A proximal end of the second tube forming the second inflation lumen may be spaced from the first outlet of the first inflation lumen. When a stent or stent graft is disposed on the balloon over the second tube, it provides a conduit for delivering inflation fluid supplied to a proximal portion of the balloon by the first outlet of the first inflation lumen to a distal portion of the balloon associated with the second outlet of the tube such that, when the balloon is inflated, the stent or stent graft is expanded. The second tube may be longer than the stent or stent graft, and may have a wall thickness in the range of about 0.0005 inches to about 0.0025 inches.

The balloon may defines a proximal cone, a distal cone, and a barrel between the proximal and distal cones, and wherein the second tube has a proximal end spaced from the first outlet and a length of the second tube is greater than or equal to a length of the barrel. The second inflation lumen does not receive the inflation fluid from the first outlet of the first inflation lumen. The first tube may also be connected to and support the balloon. The associated first outlet of the first inflation lumen may be located proximally of the balloon.

Another aspect of the disclosure pertains to an apparatus for performing a medical procedure using an inflation fluid, comprising an inflatable balloon including an interior and at least two inflation tubes positioned at least partially in the interior of the balloon in a side-by-side arrangement for transmitting the inflation fluid to the interior. The at least two inflation tubes comprise a first inflation tube having a first length and a second inflation tube having a second length different from the first length.

The apparatus may further include a guidewire lumen having an external surface supporting the two inflation tubes within the interior of the balloon. A stent or stent graft may also be provided on the balloon. The at least two tubes may have different sizes or comprise different materials. Each tube of the at least two tubes may include a proximal end connected to a partition positioned within an inflation lumen of a shaft supporting the balloon. A first tube of the at least two tubes may include a distal end positioned within a distal cone of the balloon and a second tube of the at least two tubes includes a distal end within a proximal cone of the balloon.

Still a further aspect of this disclosure pertains to an apparatus for performing a medical procedure using an inflation fluid. The apparatus comprises an inflatable balloon having an interior for receiving the inflation fluid and a tube including an inflation lumen having a partition therein. The partition serves to divide a single flow of the inflation fluid to a first inflation lumen having a first outlet for providing a first flow of the inflation fluid to the interior of the balloon and a second inflation lumen having a second outlet for providing a second flow of the inflation fluid to the interior of the balloon.

In one embodiment, a first tube forming the first inflation lumen has the first outlet, and extends to a distal cone of the balloon. The apparatus may further include a second tube forming the second inflation lumen and having the second outlet. The second tube may extend to a proximal cone of the balloon.

Still a further aspect of the disclosure relates to a balloon device, comprising a guidewire lumen, a balloon positioned over the guidewire lumen, and an inflation lumen in fluid communication with the balloon. A conduit within the balloon and coaxial with the guidewire lumen has an inner dimension greater than an outer dimension of the guidewire lumen. A region between the inner dimension of the conduit and the outer dimension of the guidewire lumen defines a flow path for delivering inflation fluid from a proximal section of the balloon to a distal section of the balloon.

In one embodiment, the conduit comprises a tube having a wall thickness in the range of about 0.0005 inches to about 0.0025 inches and, more particularly, about 0.0015 inches. The conduit may be free-floating over the guidewire lumen, or may be fixedly attached to the guidewire lumen. The balloon may define a proximal cone, a distal cone, and a body section between the proximal and distal cones, and wherein a length of the conduit is greater than or equal to a length of the body section. A shaft may be provided for supporting the balloon and including an inflation lumen having an outlet in communication with the balloon interior, and wherein the conduit includes a proximal end is spaced from the outlet of the inflation lumen.

A further aspect of the disclosure relates to an apparatus for performing a medical procedure using an inflation fluid, comprising a balloon having an interior capable of being inflated by the inflation fluid, said balloon having a balloon length. An implant supported by the balloon has an implant length. A tube extends within the balloon interior for transmitting the inflation fluid within the balloon, said tube having a tube length less than the balloon length and greater than the implant length.

In one embodiment, the balloon includes a proximal cone and a distal cone, and wherein the tube includes a first end within the proximal cone and a second end within the distal cone. The inflation lumen may include an outlet, and the tube includes a proximal end including an inlet for receiving the inflation fluid from the outlet of the inflation lumen.

Still another aspect of the disclosure relates to a method of inflating a balloon using an inflation fluid. The method comprises delivering the inflation fluid to the balloon through at least two inflation tubes at least partially positioned in the interior of the balloon in a side-by-side arrangement. The at least two inflation tubes may comprise a first inflation tube having a first length and a second inflation tube having a second length different from the first length. The method may further comprise delivering a first flow of the inflation fluid to a proximal cone of the balloon through the first inflation tube and delivering a second flow of the inflation fluid to a distal cone of the balloon through the second inflation tube.

Yet another aspect of this disclosure relates to a method of inflating a balloon. The method comprises delivering an inflation fluid to a partition dividing the flow into first and second portions prior to entering an interior of the balloon, delivering the first portion of the flow of the inflation fluid to a proximal cone of the balloon, and delivering the second portion of the flow of the inflation fluid to a distal cone of the balloon. The step of delivering the first portion of the flow may be completed using a first tube connected at a proximal end to the partition and terminating in the proximal cone. The step of delivering the second portion of the flow may be completed using a second tube connected at a proximal end to the partition and terminating in the distal cone.

Another aspect of the disclosure relates to a method of inflating a balloon, comprising providing a balloon device including a balloon positioned over a guidewire lumen, and a conduit coaxial with the guidewire lumen within the balloon, an inner dimension of the conduit greater than an outer dimension of the guidewire lumen, a region between the inner dimension of the conduit and the outer dimension of the guidewire lumen defining a fluid flow path from a proximal section of the balloon to a distal section of the balloon. The method further includes the step of transmitting fluid through an inflation lumen in fluid communication with the balloon, a portion of the fluid traveling through the fluid flow path such that a proximal section of the balloon and a distal section of the balloon are concurrently inflated.

Another aspect of the disclosure pertains to an intraluminal prosthesis comprising a stent architecture including a plurality of stent cells, the stent cells including a series of stent elements repeating in a circumferential direction. The stent elements include a plurality of first, v-shaped stent elements having a first leg portion, a second leg portion, and a peak portion, the v-shaped stent elements having at least four different orientations, and a plurality of second v-shaped stent elements connecting adjacent first v-shaped stent elements such that the second leg portion of each of the first v-shaped stent elements is connected to a second v-shaped element, the second leg portion of each of the first v-shaped stent elements narrowing in width toward the second v-shaped stent element. A plurality of connectors may connect adjacent stent elements.

In one embodiment, the first leg portion of each of the first v-shaped stent elements is parallel to a longitudinal axis of the prosthesis. The peak portion of a first orientation of the first v-shaped stent element is longitudinally spaced a distance from the peak portion of a second orientation of the first v-shaped stent element, wherein the first orientation and second orientation are adjacent to one another. The peak portion of each of the four orientations of the first v-shaped stent element may be longitudinally spaced a distance from the peak portion of an adjacent first v-shaped stent element.

The distance may be in the range from about 0.005 inch to about 0.035 inch and, more particularly, about 0.012 inch.

BRIEF DESCRIPTION OF THE DRAWING FIGURES

Figure 2:
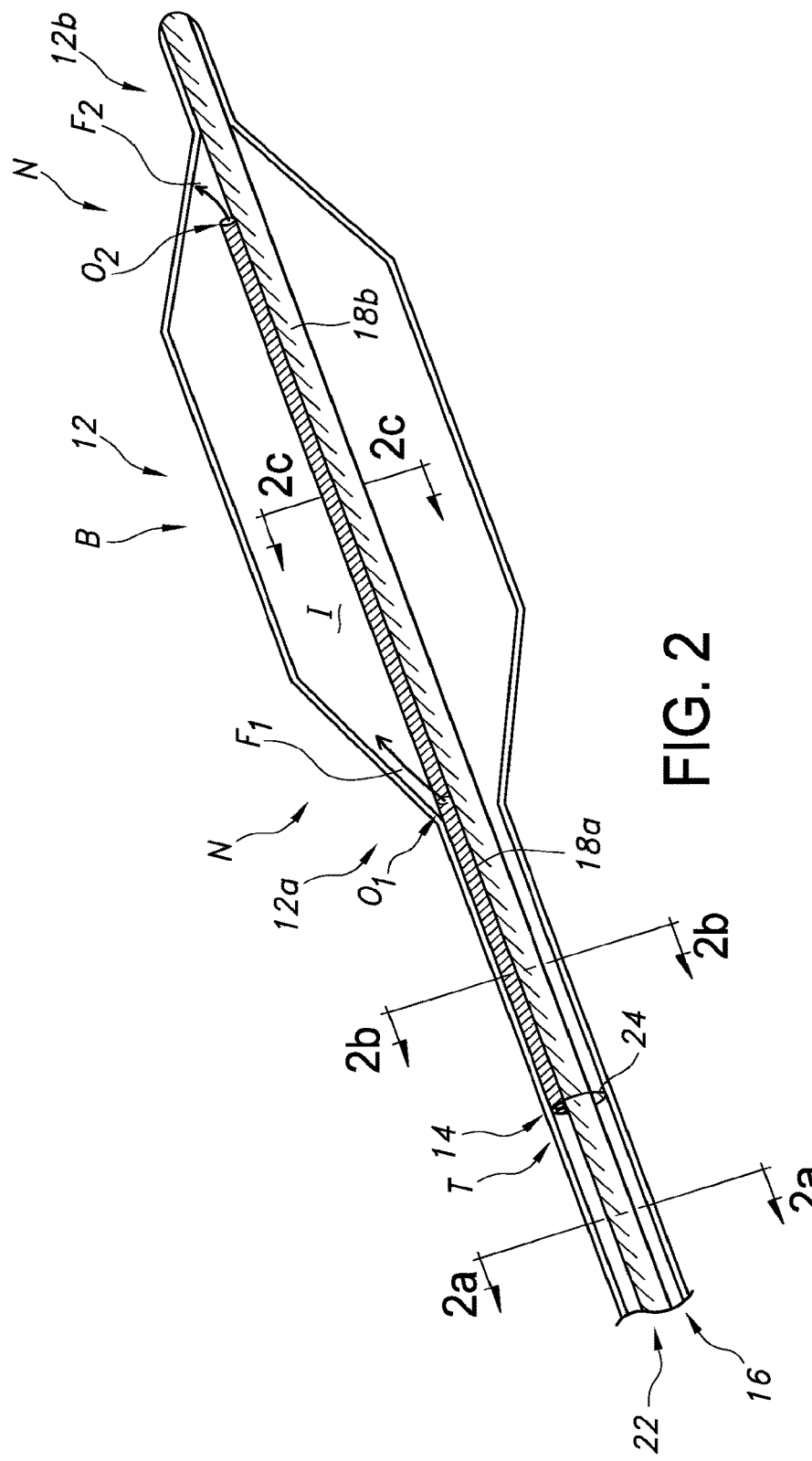
FIG. 2 is a partially cutaway perspective view of a balloon catheter according to the disclosure.
Figure 2C:
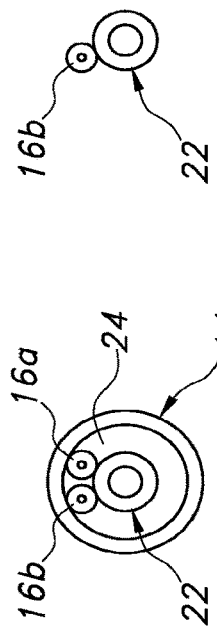
Figure 2B:
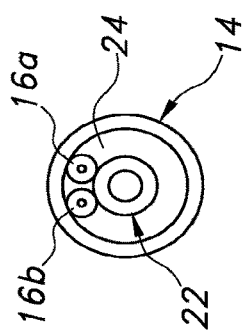
Figure 2A:
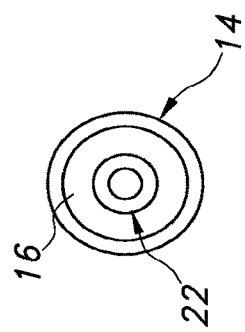
Figure 3:
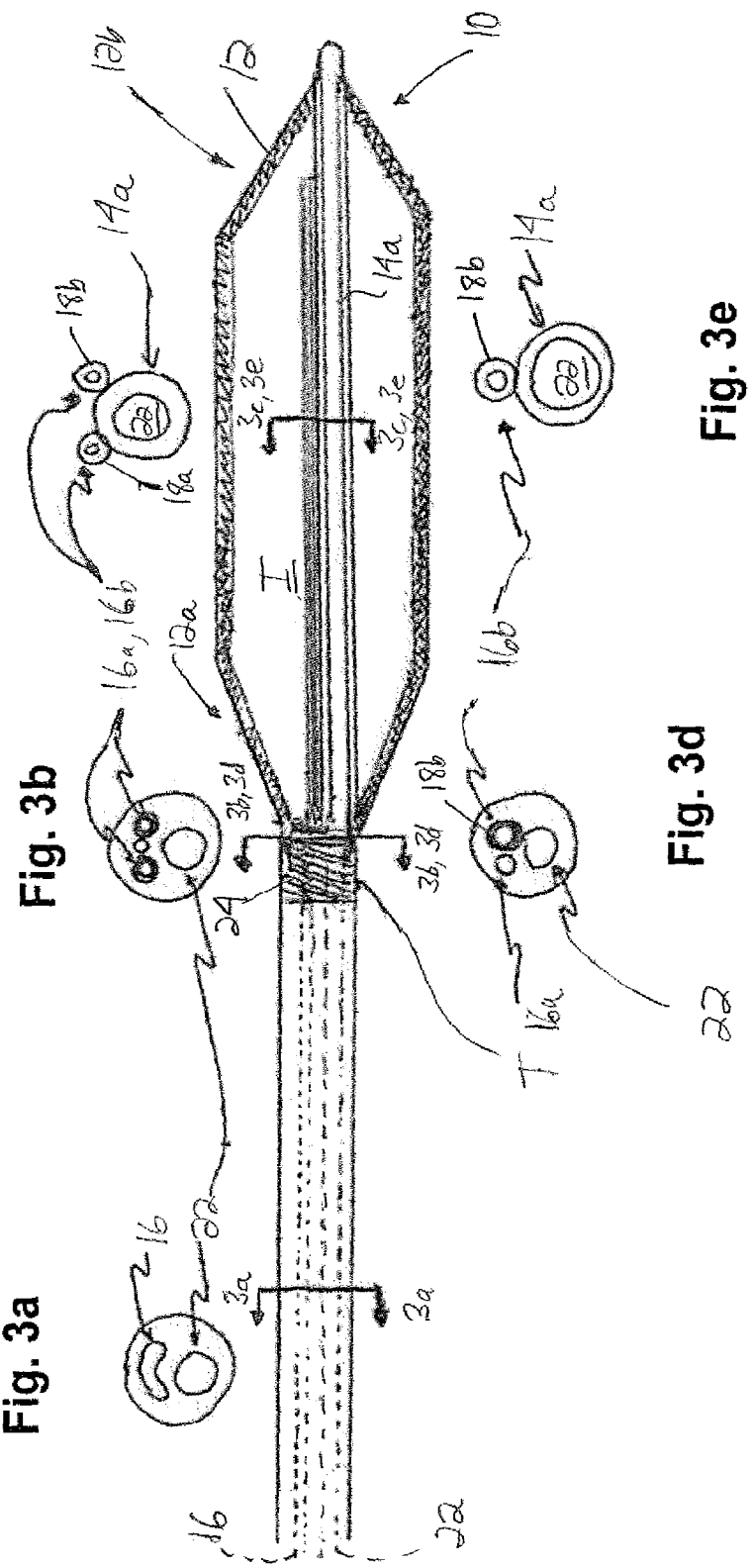
Figure 7:
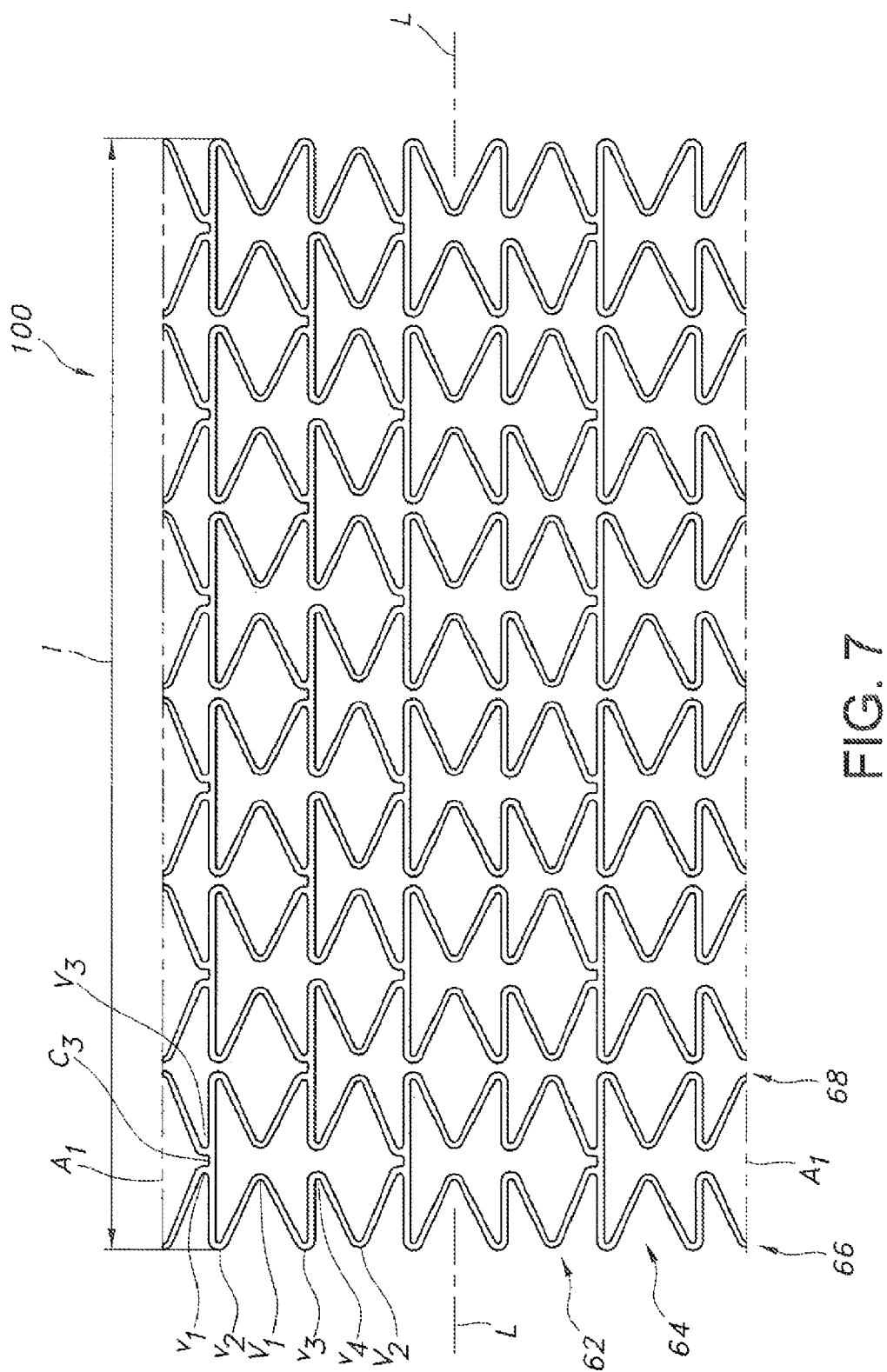

FIGS. 2a, 2b, and 2c are cross-sectional views taken along lines 2a-2a, 2b-2b, and 2c-2c of FIG. 2;

FIG. 3 is a partially cutaway side view of a balloon catheter according to the disclosure;

FIG. 3a is cross-sectional view taken along lines 3a-3a of FIG. 3;

FIGS. 3b and 3c are cross-sectional views illustrating one embodiment, taken along lines 3b-3b and 3c-3c of FIG. 3;

FIGS. 3d and 3e are cross-sectional views illustrating one embodiment, taken along lines 3d-3d and 3e-3e of FIG. 3;

FIG. 4 a partially cutaway perspective view of a balloon catheter according to the disclosure, with the balloon in an expanded condition;

FIG. 5 is a cross-sectional view taken along line 5-5 of FIG. 4;

FIG. 6 is a partially cutaway perspective view of a balloon catheter according to the disclosure, with the balloon in a folded condition;

FIG. 7 is an enlarged side view of a stent device forming another aspect of the disclosure;

FIG. 8 is another side view of the stent device; and

FIG. 9 is an enlarged side view of the stent device.

MODES FOR CARRYING OUT THE INVENTION

The description provided below and in regard to the figures applies to all embodiments unless noted otherwise, and features common to each embodiment are similarly shown and numbered.

Figure 1:
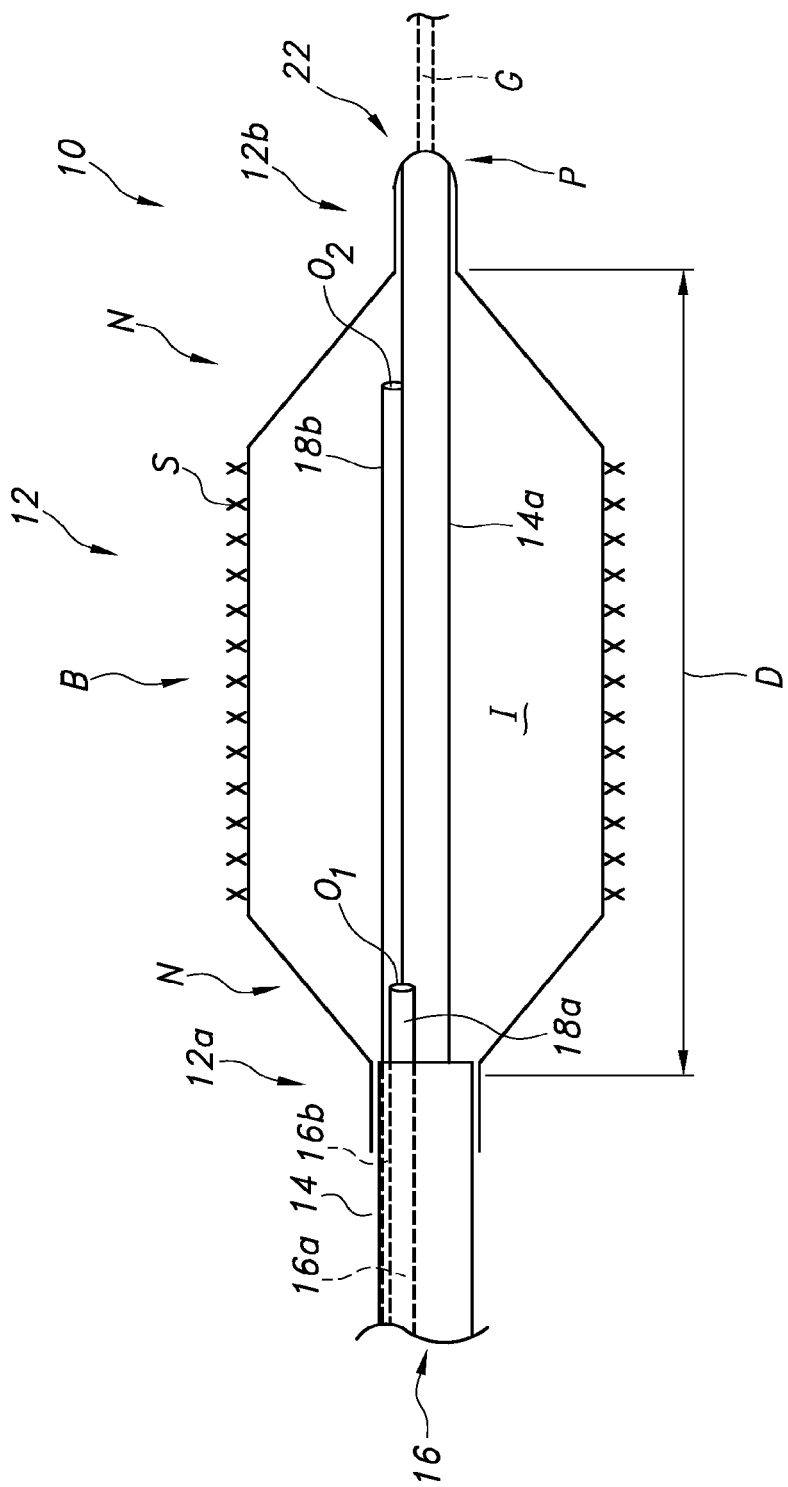
FIG. 1 is a partially cutaway side view of a balloon catheter according to one aspect of the disclosure.

Referring now to FIG. 1, an apparatus according to one aspect of the disclosure comprises a catheter 10 including an inflatable balloon 12. The balloon 12 may be mounted adjacent to a distal end of a catheter shaft in the form of a tube 14, and hence is supported thereby (even though the balloon 12 might not be directly affixed to the tube 14). A proximal end 12a and a distal end 12b of the balloon 12 may be in the form of tapered or generally conical sections or "cones" N separated by a generally cylindrical body section, or "barrel" B. Balloon 12 may include a single or multi-layered balloon wall forming the interior for receiving the inflation fluid.

The balloon 12 may be made from typical materials including polymers such as polyethylene terephthalate (PET), polyetherimide (PEI), polyethylene (PE), polytetrafluoroethylene (PTFE), expanded polytetrafluoroethylene (ePTFE), ethylene tetrafluoroethylene (ETFE), fluorinated ethylene propylene (FEP), polyoxymethylene (POM), polybutylene terephthalate (PBT), polyether block ester, polyurethane, polypropylene (PP), polyvinylchloride (PVC), poly ether-ester, polyester, polyamide, elastomeric polyamides, block polyamide/ethers, polyether block amide, silicones, Marlex high-density polyethylene, Marlex low-density polyethylene, linear low density polyethylene, polyetheretherketone (PEEK), polyimide (PI), polyphenylene sulfide (PPS), polyphenylene oxide (PPO), polysulfone, nylon, perfluoro (propyl vinyl ether) (PFA), other suitable materials, or mixtures, combinations, copolymers thereof, polymer/metal composites, and the like. The wall thickness of the balloon 12 may vary depending on the burst pressure requirements and hoop strength of the balloon material. Fibers, rods, or other types of reinforcement structures may also be included along, within, or as part of the balloon wall, which may also be provided with radiopaque qualities to allow for visualization under fluoroscopy.

The balloon 12 may be non-compliant, having a balloon wall that maintains its size and shape in one or more directions when the balloon is inflated for applying a treatment, including possibly drug or an expandable endoprosthesis (e.g., a stent S, stent graft, or similar implant device) for being positioned or deployed with the aid of catheter 10. In the case of a stent S, expansion of the balloon 12 may also result in expansion of the stent for delivery in the associated vessel or other body lumen. The stent S may be at least partially constructed of any of a variety of materials, such as stainless steel, nickel, titanium, nitinol, platinum, gold, chrome, cobalt, as well as any other metals and their combinations or alloys. In some embodiments, a stent may be at least partially constructed of a polymer material, such as a shape-memory polymer. In some embodiments, the balloon 12 or the implant carried by it may include one or more therapeutic and/or lubricious coatings.

The balloon 12 may also have a surface area that remains constant during and after inflation. The balloon 12 may also have a pre-determined length and pre-determined diameter that remain constant during and after inflation. However, the balloon 12 could be semi-compliant or compliant instead, depending on the particular use to which it is put.

The tube 14 serving as the catheter shaft includes a lumen 16 forming a conduit for supplying an inflation fluid (e.g, saline, with or without a contrast agent) from a remote source (such as an inflation device, not shown) to the balloon 12. As illustrated in FIG. 1, this inflation lumen 16 supplies the fluid to the balloon 12 via two distinct passages, thus creating independent fluid flows for inflating different portions of the balloon 12. For example, the fluid delivery may be through a first lumen 16a for delivering a first portion of the flow, and a second, distinct lumen 16b for delivering a second portion of the flow.

Each lumen 16a, 16b may be provided at a different location relative to the interior of the balloon 12. Specifically, the first lumen 16a may be formed by a first tube 18a having an outlet $O_1$ positioned at a proximal end 12a of the balloon interior I, such as adjacent to the proximal cone N when the balloon is inflated. The second lumen 16b may be formed by a second tube 18b include an outlet $O_2$ may be positioned at a distal end 12b of the balloon 12, adjacent to a second, distal cone N. It can be understood that the term "tube" is used herein to refer to a distinct structure comprising an outer wall with an inner surface forming a conduit or lumen having an inlet and outlet, and not merely a lumen within a structure.

One or both the first and second tubes 18a, 18b may be attached to the tube 14 forming the catheter shaft, or may be separate therefrom. The tube 14 may also include a guidewire lumen 22 arranged for allowing a guidewire G to pass (which may be introduced in an "over the wire" (OTW) or "rapid exchange" (RX) configuration). In either case, the guidewire lumen 22 extends fully from the proximal end 12a to a tip P adjacent the distal end 12b of the balloon 12. The guidewire lumen 22 may be provided by a smaller diameter tube 14a forming an extension or part of the tube 14 extending within the balloon interior I, which tube 14a may extend to the proximal end of the catheter 10 as well to a hub (not shown).

In one particular embodiment, as shown in FIG. 2, the catheter 10 includes a coaxial arrangement. In such an arrangement, the guidewire lumen 22 is coaxial with at least part of the inflation lumen 16 in at least the portion of the tube 14 proximal of the balloon 12 (see FIG. 2a). In this approach, a divider, such as a transverse partition 24, may be provided adjacent to (e.g., proximal of) the inlet of the dual inflation lumens 16a, 16b, and may associate with tubes 18a, 18b for transmitting flows of the inflation fluid (see FIG. 2b). Consequently, the fluid flow to the balloon 12 is divided, and enters the balloon interior I by way of a first flow $F_1$ through one lumen 16a at a first location corresponding to the outlet $O_1$ closer to the proximal end 12a and a second flow $F_2$ through another lumen 16b at a second location corresponding to the outlet $O_2$ closer to the distal end 12b (and in a side-by-side arrangement with the portion of tube 14 forming the guidewire lumen 22, see FIG. 2c).

As can be appreciated, the inflation fluid may thus be supplied in different flows to different parts of the balloon 12 in a strategic manner by selecting the length and diameter of the different tubes 18a, 18b. This allows for the relative inflation of the balloon 12 to be precisely controlled, unlike in arrangements where the fluid may enter the balloon at either the proximal end or distal end. Such precision control may help to avoid the differential inflation characteristics that result in misplacement or misalignment of a corresponding payload, such as a stent, stent graft, or other treatment, carried thereon.

In one embodiment, as shown in FIG. 3, the catheter 10 with multiple inflation passages for delivering flows of the inflation fluid to the balloon 12 is a dual lumen configuration. The catheter tube 14 thus includes a guidewire lumen 22 (which may extend though the entire balloon 12) and a separate inflation lumen 16. This inflation lumen 16 (which is shown in FIG. 3a as having an oblong curved or crescent shape in a transverse direction when viewed in cross-section) may also separate into two or more inflation lumens 16a, 16b. This division may occur at a transition T created by a divider, such as the transverse partition 24 within the inflation lumen 16 located proximally of the proximal end 12a of the balloon 12. Hence, the flow of the inflation fluid may be divided prior to entering the interior of the balloon 12.

While FIG. 3 illustrates a single catheter 10, the arrangement of the dual lumens 16a, 16b may be different in different embodiments, as shown in the cross-sections. For example, in one embodiment, as shown in FIGS. 3b and 3c, two separate tubes 18a, 18b create the dual inflation lumens 16a, 16b, and are supported within the balloon 12 along the external surface of the tube 14a forming the guidewire lumen 22. In another, as shown in FIGS. 3d and 3e, a first lumen 16a is provided adjacent the proximal end of the transition T (such as by simply forming a hole in the structure serving as partition 24), and the other lumen 16b corresponds to a separate tube 18b that extends into and at least partially through the interior I of the balloon 12. As can be appreciated, the length of the portion of the tube or tubes 18a, 18b within the balloon 12 may be less than the length D of the balloon 12 in the longitudinal direction (which balloon length D may be considered herein the distance between the end of the cone N at the distal end 12b, and the end of the cone N at the proximal end 12a).

As should be appreciated, the ability to provide multiple inflation lumens 16a, 16b comprising different sizes or lengths of tubes 18a, 18b, allows for the inflation of the balloon 12 to be controlled in an optimal manner. Specifically, the locations of the outlets $O_1$, $O_2$ may be selected to correspond to the desired inflation profile, which in most cases involves inflating the proximal and distal cones N of the balloon 12 at a substantially equal rate using different flows of fluid so as to ensure the proper deployment of an expandable implant, such as a stent or stent graft (if present), or the even application of a treatment, such as a drug. In the dual lumen embodiment, a single inflation lumen 16b may extend to the cone N at the distal end 12b of the balloon 12, while the outlet of the proximal inflation lumen 16a may simply be provided at a transition T without extending into the interior of the balloon 12. Consequently, a lower profile catheter 10 may be provided. Furthermore, the materials of the corresponding tubes 18a, 18b may be selected to provide different characteristics in terms of flexibility and strength.

The relative diameters of the lumens 16a, 16b may also be selected to control the relative amount of the inflation fluid delivered to different interior portions of the balloon 12. For example, a larger diameter tube 18b may be used to deliver the inflation fluid to the distal end 12b, while a slightly smaller tube 18a may be used to deliver the inflation fluid to the proximal end 12a, thus accounting for the pressure differential created as a result of the additional travel distance. Likewise, varying the length of one or both of the tubes 18a, 18b allows for precision control of the location of the corresponding outlets $O_1$, $O_2$, which means that the inflation fluid upon exiting may create a more pronounced effect at corresponding locations of the balloon 12 (such as within the cones N at the proximal and distal ends 12a, 12b of the balloon 12 to help prevent the undesirable condition of "watermelon seeding" mentioned in the foregoing discussion). As a consequence of this multi-level, enhanced adaptability, an optimal inflation profile may be provided, which may help to avoid the problems created by differential inflation, especially when the balloon carries a treatment, such as a stent, stent graft, drug, or any combination of the foregoing.

While the use of one or two tubes 18a, 18b is illustrated, more than two tubes may be used while achieving the desired objective of substantially even inflation. For example, a third tube may be provided for delivering inflation fluid to the middle cylindrical section, or barrel B, of the balloon 12. Likewise, pairs of tubes may be provided for delivering the inflation fluid to the balloon interior I, such as at or near the proximal and distal cones N.

FIG. 4 shows a catheter 10 also including an expandable endoprosthesis, such as a stent S or stent graft having a length E length less than the balloon length D. FIG. 5 is a cross-sectional view showing one possible construction of the tube 14 to include an inflation lumen 16, as well as a guidewire lumen 22 formed by tube 14a extending fully from the proximal end 12a to the tip P adjacent to the distal end 12b of the balloon 12. The inflation lumen 16 opens into the proximal end 12a of the balloon 12, which may be connected to the tube 14 forming the catheter shaft at the proximal end 12a and to the tip P receiving the guidewire lumen 22 at the distal end 12b.

With combined reference to FIGS. 4 and 6, it can be understood that a conduit 30 for transmitting the inflation fluid (e.g., contrast media) is provided within the balloon 12 over the guidewire lumen 22, which is partially shown in phantom. Hence, the inflation lumen fined between the inner surface of the tube forming the conduit 30 and the tube forming the guidewire lumen 22 may be annular. Consequently, when the stent or other implant is in a compressed or unexpanded condition (S') on a folded balloon (12'), fluid is able to flow into the conduit 30 from the inlet opening adjacent to the proximal end 12a of the balloon 12, and to the outlet opening adjacent to the distal end 12b. As such, the mounted stent S' remains stationary on the balloon 12 throughout insertion and inflation, and the watermelon seeding condition may be avoided.

The conduit 30 may be a thin-walled tube positioned along the guidewire lumen 22, and may be positioned over the corresponding portion of the tube 14 forming at least part of the guidewire lumen as illustrated. In this particular embodiment, the conduit 30 and the guidewire lumen 22 are co-axial, but it should be appreciated that the conduit could take the form of an auxiliary tube carried on the tube 14 within the balloon 12 in a non-coaxial or side-by-side configuration as well. It can also be appreciated from the illustrated embodiment that the conduit 30 is not directly connected to the inflation lumen 16, which may terminate at the end of the tube 14 forming catheter shaft adjacent to the proximal end 12a of the balloon 12. The conduit 30 thus includes an open end or inlet closer to or at the proximal end 12a of the balloon 12, and may further include an open end or outlet closer to or at the distal end 12b of the balloon 12.

The wall thickness of the thin-walled tube forming the conduit 30 in one embodiment is in the range of about 0.0005 inches to about 0.0025 inches, and may be about 0.0015 inches. As can be appreciated, positioning the thin-walled tube or conduit over tube 14 including the guidewire lumen 22 to which the balloon 12 is attached at a proximal end 12a and distal end 12b, enables the concurrent inflation of both distal and proximal balloon cones N, preventing the implant (e.g., stent S) from migrating. The conduit 30 may be used on a wide variety of existing catheter assemblies to provide a balloon catheter 10 with an improved inflation mechanism as compared with the case where a single flow of inflation fluid is used.

The conduit 30 may be coupled to the portion of the portion of the tube 14 forming the guidewire lumen 22 within the balloon 12 in any of a number of suitable ways. For example, in one embodiment, the conduit 30 may be free-floating over the guidewire lumen 22, such that it essentially becomes slidable along it in both directions along a longitudinal axis. In another embodiment, the conduit 30 is attached at one or more points along an outer surface of the tube 14 forming the guidewire lumen 22, whether co-axial or not.

In the co-axial configuration, the conduit 30 may have an internal dimension slightly greater than an outer dimension of the guidewire lumen 22 or tube 14a over which it is disposed. In one possible embodiment, the difference between the inner diameter of the conduit 30 and the outer diameter of the tube 14a is 0.008 inches. This configuration enables the inflation fluid to flow through the crimped stent S without affecting the profile of the balloon 12 in a significant way (at least until sufficient pressure is created to cause expansion).

The length of the conduit 30 may vary, and may be longer than the length of the body section or barrel B between the cones N at the proximal and distal ends 12a, 12b. In such case, the conduit 30 on both proximal and distal ends thereof extends, respectively, into the proximal and distal cones N (and possibly to a point of interface with the inflation lumen, but in the illustrated embodiment the two structures are spaced apart in the longitudinal direction). Considering that each of the proximal and distal cones N has a length, in one embodiment, the conduit 30 is of sufficient length to extend into each of the proximal and distal cones to approximately the mid-point of the length of the proximal and distal cones. It should be appreciated that the length of the conduit 30 may be greater than the length E of the implement, such as stent S, disposed over the balloon 12, but less than the length D of the balloon 12 itself. As a result of the compression or crimping of a stent S onto the balloon 12, the ends of the conduit 30 beyond the perimeter of the stent S may tend to flare outwardly, which flared ends further help to provide a stent retention function during insertion and prior to deployment. However, expansion of the balloon 12 removes the compressive force, and thus the ends of the conduit 30 return to normal and do not cause any hang-up that would preclude proper deployment of the stent S.

FIGS. 7-9 illustrate a stent 100 with a stent architecture including v-shaped stent elements $v_1$-$v_4$, each of which include a first leg portion parallel to the longitudinal axis L, a peak portion, and a second leg portion angled with respect to the longitudinal axis, and V-shaped stent elements $V_1$-$V_2$. Beginning from the top left side of FIG. 7, a repeating series of stent elements is shown along a first side 66 of the stent cells 62 and 64. The v-shaped stent elements $v_1$, $v_2$, $v_3$, $v_4$ are similar in shape but are oriented differently from one another with respect to a circumferential axis and/or a longitudinal axis. The V-shaped stent elements $V_1$ and $V_2$ are facing in opposite directions with respect to a circumferential axis $A_1$.

The same repeating series of stent elements (arranged identically with respect to the circumferential axis $A_1$ and longitudinal axis L) proceeds along a second side 68 of the stent cells 62 and 64, but is offset such that the sequence begins with stent element $v_3$ which is directly adjacent $v_1$ of the series along the first side 66. Thus, beginning from the top of FIG. 7 along second side 68, the series of stent elements is $v_3$, $v_4$, $V_2$, $v_1$, $v_2$, $V_1$, $v_3$, etc. Stated differently, the circumferential pattern may be considered as an M-shape, followed by a W-shape sharing a common leg with the M-shape, which is then repeated (as well as with the common leg).

The first side 66 may be connected to the second side 68 via connectors $C_3$. For instance, stent element $v_1$ of the first side 66 may be connected to stent element $v_3$ of the second side 68 at each instance along the circumferential axis $A_1$ in which stent elements $v_1$ and $v_3$ are adjacent one another. The connectors $C_3$ are attached to the stent elements $v_1$ and $v_3$ at about a peak portion thereof to align with the first leg portion thereof that is parallel to the longitudinal axis L. In stent 100, the connectors $C_3$ have a width equal to the width of the first leg portions of $v_1$ and $v_3$. The side of stent elements adjacent to the second side 68 (toward the middle of the stent 100) are connected to the second side 68 in the same manner (that is, stent elements $v_1$ and $v_3$ are connected by connectors $C_3$ at locations where the peak portion of $v_1$ is adjacent the peak portion of $v_3$). This pattern may continue along the length of the stent 100.

It is noted that stent elements $v_2$ and $v_4$ are not connected to one another by any connector when the peak portions thereof are adjacent one another. In other embodiments, these peak portions are connected by a connector. In yet other embodiments, instead of stent 100 including only connectors $C_3$, other connector types could be utilized. In still other embodiments, the connectors could connect $V_1$ and $V_2$ instead of, or in addition to connecting $v_1$ and $v_3$ and/or $v_2$ and $v_4$. For example, in one embodiment, a straight connector could connect $V_1$ and $V_2$ at locations where the peak portions thereof are facing away from each other (i.e., across stent cell 62). In one embodiment, the peaks connected by one or more of the connectors $C_3$ could be touching, such that the effective length of one or more of the connectors $C_3$ is zero.

FIG. 8 shows stent 100 after the pattern has been cut into a tube. In one embodiment, the tube forming the stent 100 is a metal tube that is laser machined to form the repeating series of stent elements. In one embodiment, the stent has a diameter of about 6 millimeters and a thickness of about 0.0085 inch after electro-polishing. In an embodiment in which the stent 100 is covered by one or more graft layers, the stent 100 can be expanded to a larger diameter for covering with the graft layer(s), can be covered with the graft layer(s) at the cut diameter, or can be crimped to a smaller diameter for covering with the graft layer(s), following post processing steps such as, for example, electro-polishing.

In the embodiment of FIGS. 7-9, the width of selected portions of the stent elements $v_1$-$v_4$ is tapered to a narrowed width for stent elements $V_1$-$V_2$ to promote uniform expansion of the stent. Such uniform expansion is particularly preferred for stents covered by graft material to avoid tearing or deformation of the graft material upon deployment. In other embodiments, the thickness of selected stent elements is reduced instead of, or in conjunction with, the tapered and narrowed of the widths thereof. In FIG. 9, widths $w_6$-$w_9$ are shown at different locations on the stent cells. Width $w_6$ is at the beginning of second leg portion of stent element $v_2$, width $w_7$ is along the length of first leg portion of stent elements $v_1$ and $v_2$, width $w_8$ is at a section of stent element $V_1$, and width $w_9$ is at a section of connector $C_3$. In the embodiment shown, the widths of $w_6$, $w_7$, and $w_9$ are the same, and the width of $w_8$ is less than the widths of $w_6$, $w_7$, and $w_9$. It is noted that the first leg portions and peak portions of stent elements $v_1$-$v_4$ have the same width along the length thereof (i.e., $w_6$, $w_7$), but second leg portions of each of stent elements $v_1$-$v_4$ taper from width $w_6$ to width $w_8$ along the length thereof. In one embodiment, which could be used in a vessel diameter of about 5 mm to about 15 mm, the widths of $w_6$, $w_7$ and $w_9$ are in the range from about 0.0070 inch to about 0.0120 inch, for example about 0.0095 inch, and the width at $w_8$ is in the range from about 0.0040 inch to about 0.0090 inch, for example about 0.0065 inch. For smaller or larger vessels, dimensions can be accordingly smaller or larger.

In FIG. 9, the peak portions of the stent elements $v_1$-$v_4$ are shown longitudinally spaced a distance $D_3$ from the peak portions of $V_1$ and $V_2$, which in one embodiment at a diameter of about 6 millimeters is in the range from about 0.005 inch to about 0.035 inch, for example about 0.018 inch. In other embodiments, the peak portions are circumferentially aligned. Also in FIG. 9, the peak portions of the stent elements $v_2$ and $v_4$ are shown longitudinally spaced, respectively, a distance $D_4$ from the peak portions of the stent elements $v_3$ and $v_1$, which in one embodiment at a diameter of about 6 mm is in the range from about 0.005 inch to about 0.035 inch, for example about 0.012 inch. The distance $D_4$ provides increased spacing for the unconnected peaks to allow additional room for expansion to better ensure that the unconnected peaks do not come into contact during delivery and/or deployment.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent to cover those variations as well.

The invention claimed is:

1. An apparatus comprising:
an inflatable balloon having proximal and distal cones and an interior for receiving inflation fluid;
a first tube comprising a first inflation lumen with a first outlet for transmitting a first flow of the inflation fluid to the interior of the balloon; and
a second tube inside the balloon having a proximal end, a distal end, a second outlet spaced from the first outlet in a longitudinal direction, and a passage between the proximal and distal ends adapted to transfer inflation fluid to the second outlet for inflating the balloon;
wherein the proximal end is located within the proximal balloon cone and the distal end is located within a distal balloon cone.

2. The apparatus of claim 1 wherein the balloon comprises any one or any combination of a therapeutic agent, a stent, or a stent graft.

3. The apparatus of claim 2 further comprising a stent or stent graft disposed on the balloon, and wherein
the first tube supplies inflation fluid to the proximal cone and to the second tube, and
the second tube supplies inflation fluid to the distal cone.

4. The apparatus according to claim 3
wherein
the proximal end spaced from the first outlet
and
the second tube is longer than the stent or stent graft.

5. The apparatus according to claim 4 wherein the second tube has a wall thickness in the range of 0.0005 inches to 0.0025 inches.

6. The apparatus according to claim 5 wherein the balloon further comprises a barrel between the proximal and distal cones, and the proximal end is spaced from the first outlet and a length of the second tube is greater than or equal to a length of the barrel.

7. The apparatus according to claim 6 wherein the first outlet is located proximally of the balloon distal cone.

8. The apparatus of claim 7 further comprising a guidewire tube, wherein the guidewire tube supports both the first tube and the second tube within the balloon.

9. The apparatus of claim 8 wherein the first tube extends into the balloon beyond a point at which the balloon is attached to a catheter shaft forming the tube.

10. The apparatus of claim 1 further comprising a stent or stent graft disposed on the balloon,
and wherein
the first tube supplies inflation fluid to the proximal cone and to the second tube, and
the second tube supplies inflation fluid to the distal cone.

11. The apparatus according to claim 1 further comprising a stent or stent graft disposed on the balloon,
and wherein
the second tube has a first proximal end spaced from the first outlet, and
the second tube is longer than the stent or stent graft.

12. The apparatus according to claim 11 wherein the second tube has a wall thickness in the range of 0.0005 inches to 0.0025 inches.

13. The apparatus according to claim 12 wherein
the balloon further comprises a barrel between the proximal and distal cones,
and
the proximal end is spaced from the first outlet and a length of the second tube is greater than or equal to a length of the barrel.

14. The apparatus according to claim 13 wherein the first outlet is located proximally of the balloon distal cone.

15. The apparatus of claim 14 further comprising a guidewire tube, wherein the guidewire tube supports both the first tube and the second tube within the balloon.

16. The apparatus of claim 15 wherein the first tube extends into the balloon beyond a point at which the balloon is attached to a catheter shaft forming the tube.

17. An apparatus comprising:
an inflatable balloon having proximal and distal cones and an interior for receiving inflation fluid;
a first tube comprising a first inflation lumen with a first outlet for transmitting a first flow of the inflation fluid to the interior of the balloon;
a second tube inside the balloon having a proximal end, a distal end, and a solid wall defining a passage between the proximal and distal ends; and
a guidewire tube, wherein the guidewire tube supports both the first tube and the second tube within the balloon.

18. An apparatus comprising:
an inflatable balloon having proximal and distal cones, proximal and distal necks, and an interior for receiving inflation fluid;
a first tube comprising a first inflation lumen with a first outlet for transmitting a first flow of the inflation fluid to the interior of the balloon; and
a second tube inside the balloon having a proximal end, a distal end, a solid wall defining a passage between the proximal and distal ends, and a second outlet spaced proximally of the distal neck;
wherein the balloon further comprises a barrel between the proximal and distal cones, the proximal end of the second tube is spaced from the first outlet, and a length of the second tube is greater than or equal to a length of the barrel;
wherein the proximal end is located within the proximal balloon cone or the proximal balloon neck.

* * * * *